United States Patent
Sanz Herranz et al.

(10) Patent No.: US 12,257,271 B2
(45) Date of Patent: Mar. 25, 2025

(54) *HOLDERMANELLA* SP. BACTERIUM AND USE THEREOF

(71) Applicant: CONSEJO SUPERIOR DE INVESTIGACIONES CIENTÍFICAS (CSIC), Madrid (ES)

(72) Inventors: Yolanda Sanz Herranz, Valencia (ES); Inmaculada Lopez Almela, Valencia (ES); Eva Ma Gomez Del Pulgar Villanueva, Valencia (ES); Alfonso Benitez-Paez, Valencia (ES); Marina Romani Perez, Valencia (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 60 days.

(21) Appl. No.: 17/418,005

(22) PCT Filed: Dec. 24, 2019

(86) PCT No.: PCT/ES2019/070882
§ 371 (c)(1),
(2) Date: Jun. 24, 2021

(87) PCT Pub. No.: WO2020/136301
PCT Pub. Date: Jul. 2, 2020

(65) Prior Publication Data
US 2022/0072064 A1    Mar. 10, 2022

(30) Foreign Application Priority Data
Dec. 26, 2018 (ES) .............................. ES201831282

(51) Int. Cl.
*A61K 35/74* (2015.01)
*A23L 33/135* (2016.01)
*A61P 3/04* (2006.01)
*A61P 3/10* (2006.01)

(52) U.S. Cl.
CPC ............ *A61K 35/74* (2013.01); *A23L 33/135* (2016.08); *A61P 3/04* (2018.01); *A61P 3/10* (2018.01)

(58) Field of Classification Search
CPC ......... A61K 35/74; A23L 33/135; A61P 3/04; A61P 3/10
See application file for complete search history.

(56) References Cited

FOREIGN PATENT DOCUMENTS

| | | | |
|---|---|---|---|
| CN | 101590081 A | 12/2009 | |
| WO | WO-2013175038 A1 * | 11/2013 | ............. A23C 9/152 |

OTHER PUBLICATIONS

McGonigle et al. "Animal models of human disease: Challenges in enabling translation", Biochemical Pharmacology, 2014, vol. 87, pp. 162-171. (Year: 2014).*
Donath et al. "Cytokines and β-Cell Biology: from Concept to Clinical Translation", Endocrine Reviews, 2008, vol. 29, No. 3, pp. 334-350. (Year: 2008).*
Bianchi et al. "Gut microbiome approaches to treat obesity in humans", Applied Microbiology and Biotechnology, 2019, vol. 103, pp. 1081-1094; first available online Dec. 6, 2018. (Year: 2018).*
English Machine Translation of WO 2013/175038 A1 published on Nov. 28, 2013, obtained from Espacenet on Jan. 23, 2023 (https://worldwide.espacenet.com/) (Year: 2013).*
Liu et al. "Incretin-based therapies for patients with type 1 diabetes: a meta-analysis", Endocrine Connections, 2019, vol. 8, Issue 3, pp. 277-288. (Year: 2019).*
George et al. "Lean diabetes mellitus: An emerging entity in the era of obesity", World Journal of Diabetes, 2015, vol. 6, No. 4, pp. 613-620. (Year: 2015).*
Šebeková et al. "Lean insulin-resistant young adults display increased cardiometabolic risk: A retrospective cross-sectional study", Diabetes Research and Clinical Practice, 2022, vol. 185, article 109217. (Year: 2022).*
Bianchi et al., "Gut microbiome approaches to treat obesity in humans", Applied Microbiology and Biotechnology, 2019, vol. 103, Issue 3, pp. 1081-1094.
Jayasinghe et al., "The New Era of Treatment for Obesity and Metabolic Disorders: Evidence and Expectations for Gut Microbiome Transplantation", Frontiers in Cellular and Infection Microbiology, 2016, vol. 6, Article 15, 11 pages.
Lesmes U et al., "Effects of resistant starch type III polymorphs on human colon microbiota and short chain fatty acids in human gut models", Journal of Agricultural and Food Chemistry, 2008, vol. 56, Issue 13, pp. 5415-5421.
Gibson, "Use of a three-stage continuous culture system to study the effect of mucin on dissimilatory sulfate reduction and methanogenesis by mixed populations of human gut bacteria", Appl Environ Microbiol., 1988, vol. 54, Issue 11, pp. 2750-2755, 6 pages.
Amandine Everard, "Cross-talk between Akkermansia muciniphila and intestinal epithelium controls diet-induced obesity", Journal, 2013, 9066-9071, vol. 110, No. 22, PNAS.
Koji Hosomi, "Oral administration of Blautia wexlerae ameliorates obesity and type 2 diabetes via metabolic remodeling of the gut microbiota", Article, 2022, 1-17, vol. 13, Nature Communications.
Silvia Moreno-Fernandez, "High Fat/High Glucose Diet Induces Metabolic Syndrome in an Experimental Rat Model", Article, 2018, 1-15, vol. 10, Nutrients.

(Continued)

*Primary Examiner* — Louise W Humphrey
*Assistant Examiner* — Deepa Mishra
(74) *Attorney, Agent, or Firm* — Hayes Soloway PC

(57) ABSTRACT

The present invention relates to the strain of *Holdemanella biformis* CECT 9752, its cellular components, metabolites, and secreted molecules, and to compositions comprising the aforementioned products, in addition to the use of said strain, but also to the genus *Holdemanella*, and to the species *H. biformis* for preventing alterations in energy homeostasis and glucose metabolism, including, glucose intolerance, insulin resistance, metabolic syndrome and diabetes.

8 Claims, 4 Drawing Sheets

Specification includes a Sequence Listing.

(56) References Cited

OTHER PUBLICATIONS

Theresa V. Rohm, "Inflammation in obesity, diabetes, and related disorders", Review, 2022, 31-55, vol. 55, Immunity.
Michael A. Nauck, "Incretin hormones and type 2 diabetes", Review, 2023, 1780-1795, vol. 66, Diabetologia.
Elena Valassi, "Neuroendocrine control of food intake", Review, 2008, 158-168, vol. 18, Nutrition, Metabolism & Cardiovascular Diseases.
Yan-Chuan Shi, "Pancreatic PYY Is Critical in the Control of Insulin Secretion and Glucose Homeostasis in Female Mice", Article, 2015, 3122-3136, vol. 156, No. 9, Endocrinology.

* cited by examiner

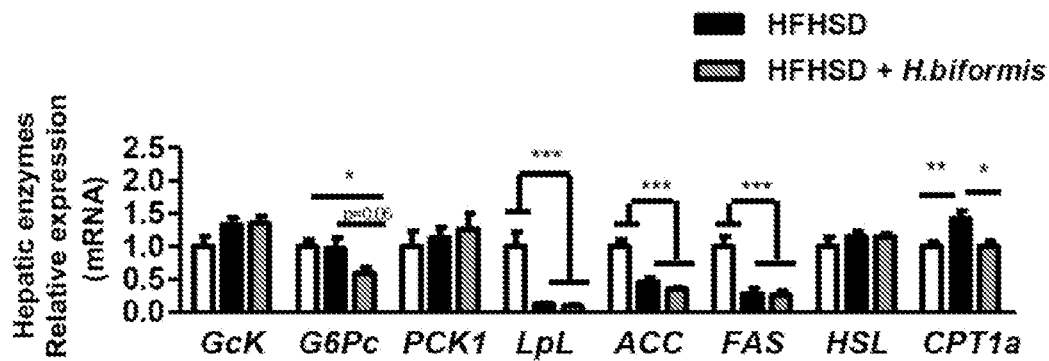
FIG. 3
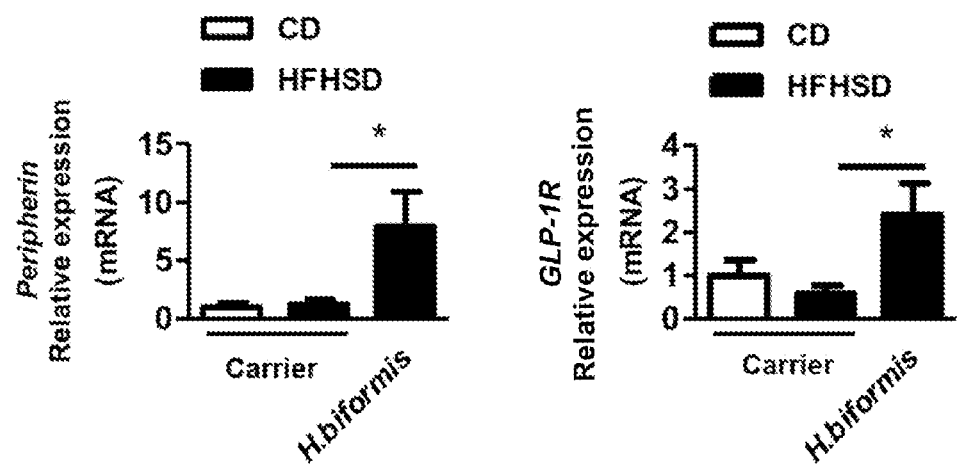
Fig. 4A
Fig. 4B

HOLDEMANELLA SP. BACTERIUM AND USE THEREOF

CROSS-REFERENCE TO RELATED APPLICATIONS AND PRIORITY

This patent application claims priority from PCT Patent Application No. PCT/ES2019/070882 filed Dec. 24, 2019, which claims priority from Spanish Patent Application No. P201831282 filed Dec. 26, 2018. Each of these patent applications are herein incorporated by reference in their entirety.

The present invention relates to the genus *Holdemanella*, to the species *Holdemanella biformis* and to the strain *H. biformis* CECT 9752, its cellular components, metabolites, and secreted molecules, and to compositions comprising the aforementioned products, as well as to the use of said strain for preventing and/or treating alterations in energy homeostasis and glucose metabolism. The present invention falls within the field of the therapeutic activity of pharmaceutical compositions or preparations, as well as within the field of food.

BACKGROUND OF THE INVENTION

Obesity currently represents a major challenge to health worldwide due to its high prevalence and comorbidities related to alterations in energy homeostasis. These comorbidities include, for example, dyslipidemia, metabolic syndrome, diabetes, cardiovascular diseases, hepatic steatosis or fatty liver, hypertension, retinopathy, and alterations in eating behaviour. These pathologies and especially those which involve alterations in glucose metabolism, such as diabetes, can also occur in non-obese subjects, although the increase in body mass is an important risk factor.

Obesity is characterised by an increase in weight and body mass mainly caused by an imbalance between intake and energy expenditure.

The neuroendocrine system regulates the energy balance through intestinal hormones which are key to controlling the intake and metabolism in different organs and tissues. Among the intestinal hormones, glucagon-like peptide 1 (GLP-1) and the peptide YY (PYY) secreted by L cells, mainly present in the distal region of the intestine, stand out. These hormones do not only have a direct effect on the distal organs (liver, adipose tissue) to control energy metabolism, but they also act as mediators in the central control of metabolism and eating habits through the neural and endocrine pathways via the gut-brain axis. GLP-1 is a peptide which suppresses appetite at the level of the hypothalamus and induces satiety, regulates glucose metabolism by inducing insulin secretion in the pancreas, reduces glucagon synthesis and reduces gastric emptying. Furthermore, GLP-1 contributes to reducing body weight, hepatic steatosis and the risk of developing diabetes and cardiovascular pathologies. PYY is more stable than GLP-1; likewise, it acts by inducing satiety and regulating glucose metabolism mainly through the reduction of gastric emptying, thus contributing to the reduction of intake and body weight. It also reduces excessive food consumption by activating proopiomelanocortin (POMC) and inhibiting neuropeptide Y (NPY) in the central nervous system.

The liver is an essential organ in the integration of endocrine, neural and nutritional signals in order to store or mobilise nutrients based on the energy demand. This integrative role makes the liver an essential organ in the maintenance of energy homeostasis and blood glucose at physiological concentrations. The metabolic activity thereof is closely controlled by insulin and other metabolic hormones. In the presence of glucose, insulin stimulates glycolysis and lipogenesis, but suppresses gluconeogenesis; in contrast, during prolonged fasting, hepatic gluconeogenesis is the main source of endogenous glucose production. The liver does not only use glucose as the main metabolic fuel, but it also uses fatty acids. The hepatocytes obtain the fatty acids from the bloodstream, which are released from adipose tissue or are absorbed from the food in the gastrointestinal tract. The fatty acids are translocated into the mitochondria through carnitine palmitoyltransferase 1 (CPT-1) in order to be metabolised by means of the beta-oxidation of the acids in order to produce Acetyl-CoA. Mitochondrial beta-oxidation does not only provide energy for the hepatocytes, but it also generates ketone bodies (β-hydroxybutyrate, acetoacetate and acetone) which are exported to the circulation and provide energy for the extrahepatic tissues. The connection of the intestine and the liver, through the portal vein, allows nutrients, hormones and metabolites of the gut microbiota to be transported. The regulation of liver metabolism can also be indirectly regulated by the intestinal tract through the central nervous system (CNS). In response to food intake, signals are transmitted through vagal afferents to the nucleus of the solitary tract (NTS) in the brain.

Preventive and therapeutic strategies based on low-calorie diets and increased physical activity represent the first option for managing obesity and its metabolic complications; however, they tend to have limited long-term effectiveness. To that end, supporting alternatives to lifestyle changes are required, which enable their effectiveness to be improved. Moreover, pharmacological strategies, including those based on GPL-1 receptor agonists for example, have side effects partly due to the fact that they are consumed continuously when used to treat chronic pathologies. Furthermore, the effectiveness thereof is limited because they are based on a single therapeutic target, without addressing the complexity of mechanisms that contribute to obesity and its complications.

Obesity and its comorbidities (type 2 diabetes, dyslipidaemia, cardiovascular disease, fatty liver, metabolic syndrome, etc.) have been associated with changes in the composition and functions of the gut microbiota in observational studies in humans, suggesting that gut microbiota could play a significant role in these disorders. This hypothesis has been confirmed by transferring the microbiota of disease or healthy individuals to new subjects and observing that the latter acquired the donor's phenotype. These experiments confirm that said changes in the microbiota, partly due to high-calorie diets, contribute to the development of obesity and its metabolic complications. This evidence has led to the development of intervention strategies in the intestinal ecosystem, such as the use of probiotics, as an alternative to improve the treatment and prevention of obesity. The products initially developed have been based on bacterial strains belonging to the genera *Lactobacillus* and *Bifidobacterium* due to their history of safe use in food. At present it is known, nevertheless, that other bacteria naturally present in a higher proportion in the human intestine, and related to a lean phenotype, could be more effective alternatives. Unlike pharmacological strategies, the use of commensal intestinal bacteria would have the advantage of being able to act through various mechanisms of action, regulating both the endocrine and neural pathways which control energy balance and, a priori, without causing adverse effects. In relation to the possible beneficial properties of the genus *Holdemanella* and the species *Holdemanella biformis* and its strains, no previous documents have been identified which demonstrate their beneficial effects on the alterations and pathologies which are the subject of the present invention.

DETAILED DESCRIPTION OF THE INVENTION

The present invention relates to the genus *Holdemanella*, to the species *Holdemanella biformis* and to the strain *H. biformis* CECT 9752 as well as its cellular components, metabolites, molecules secreted from said bacteria, and to the compositions comprising the aforementioned products, as well as to their use for preventing and/or treating alterations in energy homeostasis and glucose metabolism.

One of the beneficial effects of the bacterium object of the present invention, as well as the products derived from it, is their ability to reduce cellular and humoral mediators of inflammation, associated with obesity and dysfunctions related to glucose metabolism (for example, but not limited to, insulin resistance, metabolic syndrome and diabetes).

As seen in the in vitro assays carried out by the inventors (Example 2 of the present description), the bacteria included in the scope of the present invention induce an anti-inflammatory response in peripheral blood mononuclear cells (PBMCs), since it increases the production of the anti-inflammatory cytokine IL-4 with respect to the pro-inflammatory IFNγ, and it decreases the levels of classical monocytes (CD14++CD16−) with respect to the effects induced by the lipopolysaccharide LPS, which is an inducer of inflammation in obesity (see Table 1). The aforementioned anti-inflammatory effect can contribute to improving insulin resistance and glucose intolerance caused by the pro-inflammatory state of obesity to a greater extent than other intestinal bacteria (see Example 2).

A fundamental aspect of the invention is the ability of the genus *Holdemanella*, in particular of the species *H. biformis* and, especially, of the strain CECT 9752 to regulate the enteroendocrine system, thus contributing to the improvement of glucose metabolism and appetite regulation, which in the long term can reduce weight and body fat. Among the most significant results obtained in the in vivo assays (see Example 3), it is worth highlighting the capacity of the strains included in the scope of the invention to: (i) normalise the levels of peptide YY (PYY) and incretin GLP-1 in plasma (see FIGS. 2A, 2B); (ii) reduce basal high blood glucose induced by the high-calorie diet (see FIG. 1A) and (iii) improve glucose tolerance in an oral glucose overload test (see FIG. 1B), in mice which develop obesity and a state of pre-diabetes when fed a diet with high energy content coming from saturated fats (45%) and sugars (20%). Furthermore, the bacterium restores the insulin signalling cascade and improves the glucose uptake in the liver, as deduced from the gene expression analysis performed in this organ (see FIGS. 3 and 4A-C).

The beneficial effect of these bacteria on the maintenance or restoration of energy homeostasis and, specifically, glucose homeostasis would be applicable to individuals suffering from high blood glucose, hyperinsulinemia, glucose intolerance, insulin resistance, metabolic syndrome, type 2 diabetes, gestational diabetes, type 1 diabetes, pancreatic dysfunction, overweight, obesity, hormonal alterations, thyroiditis, liver dysfunction, hepatic steatosis, dyslipidaemia, hypertriglyceridaemia, cardiovascular pathologies, retinopathy and alterations in eating behaviour, or to individuals at risk of these alterations.

The administration thereof as a food supplement or as a drug represents important progress in the primary prevention of alterations in energy and glucose metabolism and associated chronic pathologies, the prevalence of which has tripled in the last three decades due to the excessive consumption of foods rich in fat and sugar, being one of the main causes of death in Western societies.

Therefore, in one aspect, the present invention relates to the strain *H. biformis* CECT 9752, hereinafter "strain of the invention" or "strain CECT 9752" or "strain G59".

*H. biformis* was isolated from human faeces. The strain was deposited by the Spanish National Research Council (CSIC) on 5 Nov. 2018 under the Budapest Treaty in the Spanish Type Culture Collection (CECT, calle Catedrático Agustín Escardino, 9, 46980 Paterna, Valencia, Spain). The assigned deposit number was CECT 9752.

The scientific classification of the strain of the invention is Domain Bacteria; Phylum Firmicutes; Class Erysipelotrichia; Order Clostridiales; Family Erysipelotrichaceae; Genus *Holdemanella*; Species *Holdemanella biformis*. Over time, the strain of the invention has received various names, such as "*Pseudobacterium biforme*" (Eggerth 1935) Krasil'nikov 1949, *Eubacterium biforme* (Eggerth 1935) Prevot 1938, and "*Bacteroides biformis*" Eggerth 1935. It grows in Chopped Meat Medium (DSMZ Medium 78), with 0.1% Tween 80, at 37° C., and under anaerobic conditions.

Another aspect of the present invention relates to a bacterial strain derived from the strain *H. biformis* CECT 9752, wherein the capacities described throughout the present invention are maintained or improved. The derived microorganism can be produced naturally or intentionally by mutagenesis methods known in the state of the art such as, but not limited to, the growth of the original microorganism in the presence of mutagenic or stress-causing agents, or by genetic engineering aimed at modifying specific genes. According to a preferred embodiment, the strain derived from strain *H. biformis* CECT 9752 is a genetically modified mutant. The terms "mutant strain" or "derived strain" can be used interchangeably.

The strain *H. biformis* CECT 9752 or any mutant or derivative thereof can be used in any way that exerts the described effects, such as, for example, according to a preferred embodiment of the present invention, the strain *H. biformis* CECT 9752 is in the form of viable cells (culturable or non-culturable), or according to another preferred embodiment of the invention, the strain is in the form of non-viable cells ("dead" cells inactivated by any technique known in the state of the art such as, but not limited to, heat, freezing or ultraviolet radiation).

Another aspect of the present invention relates to cellular components, metabolites, secreted molecules or any of the combinations thereof, obtained from the strain of the invention, or from a combination of microorganisms comprising at least one strain of the invention.

Cellular components of the bacterium could include components of the cell wall (such as, but not limited to, peptidoglycan), nucleic acids, components of the membrane, or others, such as proteins, lipids and carbohydrates and the combinations thereof, such as lipoproteins, glycolipids or glycoproteins. Metabolites include any molecule produced or modified by the bacterium as a consequence of its metabolic activity during its growth, the use in technological processes (for example, but not limited to, food or drug manufacturing processes), during product storage or during the gastrointestinal transit. Examples of these metabolites are, but not limited to, organic and inorganic acids, proteins, peptides, amino acids, enzymes, lipids, carbohydrates, lipoproteins, glycolipids, glycoproteins, vitamins, salts, metals or nucleic acids. Secreted molecules include any molecule exported or released to the outside by the bacterium during its growth, the use thereof in technological processes (for example, food or drug manufacturing), product storage or gastrointestinal transit. Examples of these molecules are, but not limited to, organic and inorganic acids, proteins, peptides, amino acids, enzymes, lipids, carbohydrates, lipoproteins, glycolipids, glycoproteins, vitamins, salts, metals or nucleic acids.

Another aspect of the present invention relates to a composition, hereinafter "composition of the invention", comprising the strain of the invention and/or the cellular components, metabolites, secreted molecules of the strain of the invention or any of the combinations thereof.

The composition, defined in a general way, is a set of components made up of at least the strain of the invention in any concentration; or at least the cellular components, metabolites, secreted molecules of the strain of the invention or any of the combinations thereof; or a combination thereof.

In a preferred embodiment, the composition of the invention has a concentration of the strain of the invention of between $10^3$ and $10^{14}$ colony-forming units (cfu) per gram or millilitre of final composition.

In another particular embodiment, the composition of the invention may further comprise at least another additional microorganism of the same or different genus, species or strain of the invention and/or the cellular components, metabolites or secreted molecules thereof, or any combination thereof. For example, but not limited to, the additional microorganism that can be part of said composition is selected from at least one of the following groups:

- at least one strain of another species of the genus *Holdemanella* or of the species *H. biformis*;
- at least one strain of another species of the genus *Bacteroides* or of the species *B. uniformis*;
- at least one strain of another species of the genus Phascolarctobacterium or of the species *P. faecium*;
- at least one strain of another species of the genus *Christensenella* and of the species *C. minuta*;
- at least one lactic bacterium or *Bifidobacterium* of human, food or environmental origin. The lactic bacterium is selected from the list comprising, but not limited to, a bacterium of the genus *Bifidobacterium, Lactobacillus, Lactococcus, Weissella, Pediococcus* or *Enterococcus, Propionibacterium, Leuconostoc, Streptococcus;*
- at least one strain of other phylogenetic groups, genera or species of prokaryotes of human, food or environmental origin, such as, for example, but not limited to, Archaea, Firmicutes, Bacteroidetes, Proteobacteria, Actinobacteria, Verrucomicrobia, Fusobacteria, Methanobacteria, Spirochaetes, Fibrobacteres, Deferribacteres, *Deinococcus, Thermus*, Cyanobacteria, Methanobrevibacterium, *Peptostreptococcus, Ruminococcus, Coprococcus*, Subdolingranulum, *Dorea, Bulleidia, Anaerofustis, Gemella, Roseburia, Catenibacterium, Dialister, Anaerotruncus, Staphylococcus, Micrococcus, Propionibacterium, Enterobacteriaceae, Faecalibacterium, Bacteroides, Parabacteroides, Prevotella, Eubacterium, Akkermansia, Bacillus, Butyrivibrio* or *Clostridium;*
- at least one strain of fungus or yeast, such as, for example, but not limited to, one belonging to the genus *Saccharomyces, Candida, Pichia, Debaryomyces, Torulopsis, Aspergillus, Rhizopus, Mucor* or *Penicillium*.

The additional microorganism can be a strain from the same species or from a different species or a taxonomic group of microorganisms from the one corresponding to the strain of the invention. The cells comprising the composition may be non-viable or viable and be in any phase of the development or growth state (latent, exponential, stationary, etc.), regardless of the morphology it has. In a particular embodiment, said additional microorganism comprises at least one intestinal bacterium or one lactic bacterium, particularly, one human intestinal bacterium.

Optionally, in another particular embodiment, the composition of the invention may further comprise at least one bioactive component (active substance, active ingredient or therapeutic agent), such as other food components, plant products and/or drugs.

The term "bioactive component" refers to a compound with biological activity within the scope of application of the patent which can improve or complement the activity of the strain CECT 9752, including food ingredients or components (for example, but not limited to: polyunsaturated fatty acids, conjugated linoleic acid, prebiotics, fibre, guar gum, glucomannan, chitosan, copper picolinate, calcium, etc.), other probiotics, plants, plant extracts or components and drugs.

In a particular embodiment, the composition of the invention is a pharmaceutical composition. The pharmaceutical composition is a set of components made up of at least the strain of the invention in any concentration; or at least the cellular components, metabolites, secreted molecules of the strain of the invention or any of the combinations thereof, which has at least one application in improving the physical, physiological or psychological well-being of a subject, which implies an improvement in the general state of their health or a reduction in the risk of disease. Said pharmaceutical composition can be a medicament.

The term "medicament" has a more limited meaning than the meaning of "pharmaceutical composition", as defined in the present invention, since "medicament" necessarily implies a preventive or therapeutic effect. The medicament to which the present invention relates may be for human or veterinary use. The "medicament for human use" is any substance or combination of substances that has properties for treating or preventing diseases in humans or that can be used in humans or administered to humans for the purpose of restoring, correcting or modifying physiological functions exerting a pharmacological, immune or metabolic effect, or establishing a medical diagnosis. The "medicament for veterinary use" is any substance or combination of substances that has curative or preventive properties with respect to animal diseases or that can be administered to an animal for the purpose of restoring, correcting or modifying its physiological functions exerting a pharmacological, immune or metabolic effect, or establishing a veterinarian diagnosis. "Veterinary medicaments" will also be considered "premixes for medicated feed" prepared to be incorporated into a feed.

In addition to the requirement of therapeutic efficacy wherein said pharmaceutical composition may require the use of other therapeutic agents, there may be additional fundamental reasons which oblige or recommend to a great extent the use of a combination of a compound of the invention and a bioactive component, wherein said bioactive component is attributed with appropriate activity in order to constitute a medicament. Said compound of the invention obviously refers to the strain of the invention, or the strain derived from it, or the cellular components, metabolites, secreted molecules or any of the combinations thereof, obtained from the strain of the invention.

In a particular embodiment, the pharmaceutical composition further comprises, at least, a carrier and/or an excipient, pharmaceutically acceptable.

The "carrier" is preferably an inert substance. The function of the carrier is to facilitate the incorporation of other compounds, allow better dosing and administration or to give the pharmaceutical composition consistency and shape. Therefore, the carrier is a substance that is used in the medicament to dilute any of the components of the pharmaceutical composition of the present invention to a certain volume or weight; or that, even without diluting said components, is capable of allowing better dosing and administration or giving the medicament consistency and shape. When the form of presentation is liquid, the pharmaceutically acceptable carrier is the diluent.

The term "excipient" refers to a substance that aids the absorption of any of the components of the composition of the present invention, stabilises said components or aids the preparation of the pharmaceutical composition in the sense of giving it consistency or providing flavours that make it more pleasant. Thus, excipients could have the function of holding components together, such as starches, sugars or celluloses, the function of sweetening, the function of colouring, the function of protecting the medicament, for example to isolate it from air and/or moisture, the function of filling a tablet, capsule or any other form of presentation, such as, for example, dibasic calcium phosphate, the function of disintegrating in order to facilitate the dissolution of components and the absorption thereof in the intestine, without excluding other types of excipients not mentioned herein. Therefore, the term "excipient" is defined as a material that, included in galenic forms, is added to active ingredients or to the associations thereof to allow for the preparation and stability thereof, to modify the organoleptic properties thereof or to determine the physicochemical properties of the pharmaceutical composition and the bioavailability thereof. The "pharmaceutically acceptable" excipient must allow for the activity of the compounds of the pharmaceutical composition, in other words, it is compatible with said components.

Furthermore, as understood by a person skilled in the art, the excipient and the carrier must be pharmacologically acceptable, in other words, the excipient and the carrier are allowed and evaluated so that no harm is caused to the organisms to which it is administered.

The pharmaceutical composition or medicament can be presented in any clinically permitted form of administration and in a therapeutically effective amount. For example, it may be in a form adapted for oral, sublingual, nasal, intrathecal, bronchial, lymphatic, rectal, transdermal, inhaled or parenteral administration, preferably in a form adapted for oral administration. The pharmaceutical composition of the invention can be formulated in solid, semi-solid, liquid or gaseous forms, such as a tablet, capsule, powder, granule, ointment, solution, suppository, injection, inhalant, gel, microsphere or aerosol. The form adapted for oral administration is selected from the list comprising, but not limited to, drops, syrup, herbal tea, elixir, suspension, extemporaneous suspension, drinkable vial, tablet, capsule, granulate, sachet, caplet, pellet, pill, lozenge or lyophilised form. In a particular embodiment, the composition of the invention is presented in a form adapted for oral, sublingual, nasal, bronchial, lymphatic, rectal, transdermal, inhaled or parenteral administration.

In a more particular embodiment, the composition of the invention is presented in a form adapted for oral administration. The form adapted for oral administration refers to a physical state that can allow for the oral administration thereof. Said form adapted for oral administration is selected from the list comprising, but not limited to, drops, syrup, herbal tea, elixir, suspension, extemporaneous suspension, drinkable vial, tablet, capsule, granulate, sachet, caplet, pellet, pill, lozenge or lyophilised form.

The "galenic form" or "pharmaceutical form" is the disposition to which the active ingredients and excipients are adapted in order to constitute a medicament. It is defined by the combination of the form in which the pharmaceutical composition is presented by the manufacturer and the form in which it is administered.

In the present invention, the term "therapeutically effective amount" refers to the amount of the component of the pharmaceutical composition that when administered to a mammal, preferably a human, is sufficient to produce prevention and/or treatment, as defined below, of a disease or pathological condition of interest in the mammal, preferably a human. The therapeutically effective amount will vary, for example, according to the activity of the strain of the invention; the cellular components, metabolites, secreted molecules or any of the combinations thereof, in any form of presentation; the therapeutically effective amount will also vary according to the metabolic stability and duration of action of the compound; age, body weight, general state of health, sex and diet of the patient; the mode and time of administration; the excretion rate, the combination of drugs; the seriousness of the particular disorder or pathological condition; and the patient being subjected to therapy, but this can be determined by one skilled in the art according to his or her own knowledge and that description.

Alternatively to the pharmaceutical composition, the composition of the invention can also be a nutritional composition.

The term "nutritional composition" of the present invention refers to a food that, regardless of providing nutrients to the subject who takes it, beneficially affects one or more functions of the body, in a way that provides a better state of health and well-being. Consequently, said nutritional composition can be intended for the prevention and/or treatment of a disease or of the factor causing a disease. Therefore, the term "nutritional composition" of the present invention can be used as a synonym for food with healthy properties, functional food or food for specific nutritional purposes or medicinal food.

In a particular embodiment, the nutritional composition is a food, a supplement, a nutraceutical, a probiotic or a symbiotic.

In a more particular embodiment, the food is selected from the list comprising: dairy product, plant product, meat product, snack, chocolate, beverage or baby food. The dairy product is selected from the list comprising, but not limited to, product derived from fermented milk (for example, but not limited to, yogurt or cheese) or non-fermented milk (for example, but not limited to, ice cream, butter, margarine, milk serum). The plant product is, for example, but not limited to, a grain in any form of presentation, fermented or unfermented. The beverage can be, but not limited to, any fruit juice or unfermented milk.

The term "supplement", synonymous with any of the terms "dietary supplement", "nutritional supplement", or "food supplement", is a "food ingredient" intended to supplement food. Some examples of dietary supplements are, but not limited to, vitamins, minerals, botanicals, amino acids and food components such as enzymes and glandular extracts. They are not presented as substitutes for conventional food or as a sole component of a meal or of the food diet but rather as a complement to the diet.

The term "nutraceutical" as used in the present invention refers to substances isolated from a food and used in a dosage form that have a beneficial effect on health.

The term "probiotic" as used in the present invention refers to live microorganisms that when administered in adequate amounts promote health benefits to the host organism.

The term "symbiotic" as used in the present invention refers to foods that contain a mixture of prebiotics and probiotics. As a general rule, they contain a prebiotic component that favours the growth and/or metabolic activity and ultimately the effect of the probiotic with which it is combined, such as, for example, and not limited to, the association of fructooligosaccharides or galactooligosaccharides with bifidobacteria.

Another aspect of the present invention relates to the use of the strain of the invention, or the components derived from it, or the composition of the invention, for manufacturing a medicament, a nutritional composition or a food.

Another aspect of the present invention relates to the strain CECT 9752, a cellular component, metabolite, secreted molecule or any of the combinations thereof obtained from the strain of the invention, or the composition of the invention, for the use thereof as a medicament. The term "medicament" has been previously defined, and it is applicable to the present inventive aspect.

In another aspect, the present invention relates to a bacterium of the genus *Holdemanella*, or a bacterium derived from it, a cellular component, metabolite, secreted molecule, or any of the combinations thereof, derived from a bacterium of the genus *Holdemanella*, or a composition comprising a bacterium of the genus *Holdemanella*, for the use thereof in the prevention and/or treatment of diseases related to alterations in glucose metabolism, including high blood glucose, hyperinsulinemia, glucose intolerance, insulin resistance, metabolic syndrome, type 2 diabetes, gestational diabetes, type 1 diabetes, pancreatic dysfunction, overweight, obesity, hormonal alterations, thyroiditis, liver dysfunction, hepatic steatosis, dyslipidaemia, hypertriglyceridaemia, cardiovascular pathologies and retinopathy.

In a particular embodiment, the bacterium of the genus *Holdemanella* is the species *H. biformis*, particularly, the strain *H. biformis* with deposit number CECT 9752.

In the present invention, the term "treatment" refers to fighting the effects of a disease or pathological condition of interest in a subject (preferably mammal, and more preferably human) that includes:
(i) inhibiting the disease or pathological condition, in other words, stopping its development;
(ii) alleviating the disease or pathological condition, in other words, causing the remittance of the disease or pathological condition or the symptoms thereof;
(iii) stabilising the disease or pathological condition.

In the present invention, the term "prevention" refers to preventing the onset of the disease, in other words, preventing the disease or pathological condition from appearing in a subject (preferably mammal, and more preferably a human), particularly, when said subject has a predisposition for the pathological condition.

In the present invention, "diseases related to alterations in glucose metabolism" are understood to be all those diseases in which an incorrect use of the glucose by the cells, organs or tissues can be produced in a primary or secondary manner, including high blood glucose, hyperinsulinemia, glucose intolerance, insulin resistance, metabolic syndrome, type 2 diabetes, gestational diabetes, type 1 diabetes, pancreatic dysfunction, overweight, obesity, hormonal alterations, thyroiditis, liver dysfunction, hepatic steatosis, dyslipidaemia, hypertriglyceridaemia, cardiovascular pathologies and retinopathy.

In the present invention, "glucose intolerance" is understood as the alteration developed as a consequence of the lack of production or resistance to insulin, wherein the insulin produced by the pancreas is insufficient to metabolise blood sugar, which causes the glucose level to stay high. However, even if the glucose levels are above normal, it cannot be classified as diabetes. This state is considered as "prediabetes".

In the present invention, "insulin resistance" is understood to be the condition in which the tissues have a decreased response to the action of insulin, which makes it difficult for them to have circulating glucose; especially the liver, skeletal muscle, adipose tissue and the brain. This alteration in conjunction with the deficiency of insulin production by the pancreas can lead, after some time, to the development of type 2 diabetes mellitus. The resistance to insulin is also known as insulin resistance.

In the present invention, "metabolic syndrome" is understood to be the disease comprising a group of conditions which puts the individual at risk of developing heart disease and type 2 diabetes. Examples of these conditions include, but not limited to, arterial hypertension, high blood glucose, high triglyceride blood levels, low blood levels of HDL and excess fat around the waist.

In the present invention, "type 2 diabetes" is understood to be the disease characterised by having high levels of glucose in the blood due to the pancreas not producing enough insulin or the cells not being sensitive to insulin and not being able to use it. Insulin is a hormone that helps glucose enter cells to provide them with energy. With time, a high blood glucose level can cause serious problems to the heart, eyes, kidneys, nerves, gums and teeth. Diabetes is called gestational diabetes when it appears in pregnancy.

In a particular embodiment, the invention relates to a bacterium of the genus *Holdemanella*, or a bacterium derived from it, a cellular component, metabolite, secreted molecule, or any of the combinations thereof, derived from a bacterium of the genus *Holdemanella*, or a composition comprising a bacterium of the genus *Holdemanella*, for the use thereof as an adjuvant in the treatment of any of the diseases mentioned in previous paragraphs.

In the present invention, "adjuvant" is understood as the compound which helps:
to improve the effectiveness or efficiency of other drugs for the treatment of diseases related to alterations in glucose metabolism, including high blood glucose, hyperinsulinemia, glucose intolerance, insulin resistance, metabolic syndrome, type 2 diabetes, gestational diabetes, type 1 diabetes, pancreatic dysfunction, overweight, obesity, hormonal alterations, thyroiditis, liver dysfunction, hepatic steatosis, dyslipidemia, hypertriglyceridaemia, cardiovascular pathologies and retinopathy, and/or
to decrease the frequency of administration or enhance the efficacy thereof by means of the administration of a formulation of the strain of the invention with complementary action mechanisms.

In another particular embodiment, the treatment of diabetes 2 is based on incretins. In the present invention, "incretins" are understood as a series of hormones which are produced in the intestine in response to food intake and which regulate it, as well as glucose metabolism. One of the most important effects thereof is the stimulation of insulin secretion by the pancreas and the decrease in blood glucose levels. The two main incretins are gastric inhibitory polypeptide (GIP) and glucagon-like peptide 1 (GLP-1).

In another aspect, the present invention relates to a bacterium of the genus Holdemanella, or a bacterium derived from it, a cellular component, metabolite, secreted molecule, or any of the combinations thereof, derived from a bacterium of the genus Holdemanella, or a composition comprising a bacterium of the genus Holdemanella, for preparing a food. The term medicament has been previously defined in the present description and is applicable to the present inventive aspect. In a particular embodiment of the uses of the invention, the bacterium is a genetically modified mutant.

In another particular embodiment of the uses of the invention, the bacterium is in the form of viable cells or in the form of non-viable cells.

In another particular embodiment of the uses of the invention, the composition comprises, additionally, at least one bioactive component.

In another particular embodiment of the uses of the invention, the composition comprises, additionally, at least one microorganism different than the bacterium of the genus Holdemanella, particularly, H. biformis, more particularly, H. biformis CECT 9752. In a more particular embodiment, the microorganism different than the bacterium of the genus Holdemanella is a human bacterium or a lactic bacterium.

In another particular embodiment of the uses of the invention, the composition is a pharmaceutical composition. In a more particular embodiment, the composition comprises, additionally, at least one pharmaceutically acceptable carrier and/or excipient.

In another particular embodiment of the uses of the invention, the composition is presented in a form adapted for oral, sublingual, nasal, bronchial, lymphatic, rectal, transdermal, inhaled or parenteral administration.

In another particular embodiment of the uses of the invention, the composition is a nutritional composition, more particularly, the nutritional composition is a food, a supplement, a nutraceutical, a probiotic or a symbiotic. In another even more particular embodiment, said food is selected from the list consisting of a dairy product, a plant product, a meat product, a snack, chocolate, beverage or baby food.

In another particular embodiment of the uses of the invention, the composition has a concentration of the bacterium of the genus Holdemanella of between $10^3$ and $10^{14}$ colony-forming units (cfu) per gram or millilitre of final composition.

In another particular embodiment of the uses of the invention, the bacterium of the genus Holdemanella is the species H. biformis, particularly, the strain H. biformis with deposit number CECT 9752.

Throughout the description and the claims, the word "comprises" and its variants do not intend to exclude other technical features, additives, components or steps. For those skilled in the art, other objects, advantages and features of the invention may be partially deduced from both the description and the embodiment of the invention. The following examples and figures are provided by way of illustration and are not intended to limit the present invention.

BRIEF DESCRIPTION OF THE FIGURES

FIG. 3: Effect of the administration of the strain H. biformis CECT 9752 ($1 \times 10^8$ cfu/day) to obese C57BL/6 mice (n=10/group) for 14 weeks on the enzymatic levels of energy metabolism in the liver. Relative expression of genes for: glucokinase (Gck), glucose-6 phosphatase catalytic unit (G6Pc), phosphoenolpyruvate carboxylase 1 (PcK1), lipoprotein lipase (LpL), acetyl-CoA carboxylase (ACC), fatty acid synthetase (FAS), hormone-sensitive lipase (HSL) and carnitine palmitoyltransferase (Cpt1a). Statistically significant differences were established by applying one-way ANOVA followed by the Tukey test (p<0.05) (a and b). CD, control diet; HFHSD, high-fat diet.

FIG. 4A-4C: Effect of the administration of the strain H. biformis CECT 9752 ($1 \times 10^8$ cfu/day) to obese C57BL/6 mice (n=10/group) for 14 weeks on the expression levels of (a) peripherin and (b) the receptor of GLP-1 and proglucagon (c) in the ileum. Statistically significant differences were established by applying one-way ANOVA followed by the Tukey test (p<0.05). CD, control diet; HFHSD, high-fat diet.

EXAMPLES

Figure 1A:
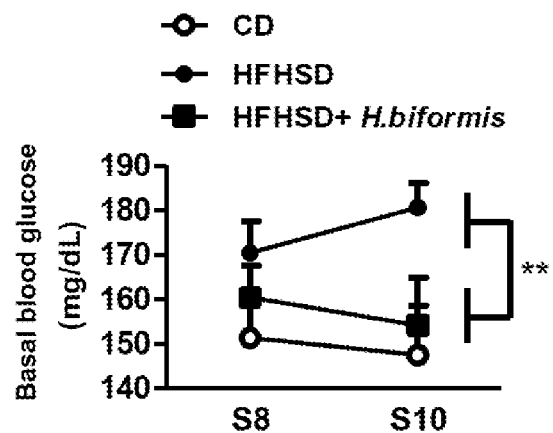
FIGS. 1A-1B: Effect of the administration of the strain H. biformis CECT 9752 ($1 \times 10^8$ cfu/day) to obese C57BL/6 mice (n=10/group) for 14 weeks on basal blood glucose and glucose tolerance. (a) Fasting blood glucose levels (mg/dl) at week 8 and 10. (b) Glucose tolerance test, blood glucose was measured at 15, 30, 60 and 120 minutes after having administered an oral glucose overload (2 g/Kg). The area under the curve (AUC) for results from the glucose tolerance test is shown. The data are represented with means and standard error. Statistically significant differences were established by applying one-way ANOVA followed by the Tukey test (p<0.05). CD, control diet; HFHSD, high-fat diet; HFHSD+H. biformis, high-fat diet+H. biformis ($1 \times 10^8$ cfu/day).

Next, the invention will be illustrated by means of assays carried out by the inventors that demonstrate the effectiveness of the product of the invention.

Example 1. Isolation and Identification of Holdemanella biformis

Different intestinal bacteria were isolated from faeces from healthy volunteers. 1.25 grams of faeces were used and diluted in 10 mM phosphate buffer with 0.05% cysteine (1:10 dilution) containing a NaCl concentration of 130 mM (PBS) and homogenised in a Lab-Blender Stomacher 400 (Seward Medical, London, 35 UK). The said dilution was inoculated in 37.5 ml of intestinal bacteria medium (IBM), the composition of which is based on the media recommended in previous publications (Gibson, G. R., et al., Appl. Environ. Microbiol., 54 (11): 2750-5, 1988; Lesmes, U et al., J. Agric. Food Chem., 56:5415-5421, 2008), with some modifications designed by the inventors:

Main ingredients: distilled water (1600 ml), peptone water (4 g), $NaHCO_3$ (4 g), $CaCl_2$) (0.02 g), pectin (4 g), xylan (4 g), wheat bran extract (4 g), arabinogalactans (2 g), gum arabic (2 g), starch (10 g), casein (6 g), inulin (2 g), NaCl (0.2 g). Autoclaved at 121° C. for 60 minutes and left to cool overnight.

Mucin solution: Mucin (8 g), distilled water (200 ml). Autoclaved 20 minutes.

Salts and vitamins: Distilled water (100 ml), $K_2HPO_4$ (0.08 g), $KH_2PO_4$ (0.08 g), $MgSO_4$ (0.02 g), hemin (0.01 g) and menadione (0.002 g).

Cysteine solution: L-cysteine-HCl (1 g), distilled water (100 ml).

The mixture of salts and vitamins with the cysteine solution were combined and 6M KOH was added until the final solution turned translucent brown and was sterilised by filtration.

The final IBM was obtained by mixing the main ingredients, the mucin solution, salts and vitamins and the cysteine solution, making up a volume of 2 L under sterile conditions.

The 50 ml of faeces diluted in IBM medium prepared by the inventors were fermented for 24 hours in an anaerobic chamber (Whitley DG250 Workstation, Don Whitley Scientific) under stirring and keeping the pH between 6.9-7.0.

The IBM medium fermented for 24 hours was filtered (through a pore size of 0.22 μm) and used as a supplement to "Fastidious Anaerobe Agar" (FAA) medium agar plates with 0.5% defibrinated blood, in which serial dilutions of the fermented faeces were inoculated (0.1 ml of inoculum of each serial dilution in each plate). This supplement of the fermented IBM medium contains substrates produced by the gut microbiota, being a medium enriched with nutrients present in the intestinal ecosystem which allows for a better recovery of autochthonous bacteria under laboratory conditions. The inoculated plates were incubated 72 hours at 37° C. in an anaerobic chamber.

Among the colonies that grew after 72 hours on the plate, *Holdemanella biformis* CECT 9752 was isolated. It was identified by sequencing the 16S rRNA gene (1.26 Kb) using the primers 27f (5'-AGAGTTTGATCCTGGCTCAG-3' (SEQ ID NO: 1)) and 1401r (5'-CGGTGTGTACAA-GACCC-3' (SEQ ID NO: 2)). The reactions after DNA amplification were purified with the Illustra GFX PCR DNA and Gel Band Purification Kits (GE Healthcare) and sequenced by Sanger technology in an ABI 3730XL sequencer (Stabvida-Caparica-Portugal). By comparing the sequences obtained with the NCBI database and the BLASTn algorithm, the identification of the isolated strain (G59) with the species *Holdemanella biformis* strain DSM 3989 (partial sequence, 16S ribosomal RNA) was obtained with 98% percent identity. 16S sequence (SEQ ID NO: 3) used for identification of identity by Blastn algorithm using oligos 27F and 1401r for the sequencing thereof:

```
CTTCATGAAGTCGGGTTGCAGACTTCAATCCGAACTGAGACGTCCTTTA
TGAGATTCGCTTGCCTTCACAGGCTTGCCGCTCTTTGTAGACGCCATTG
TAGTACGTGTGTAGCCCAGGCCATAAGGGGCATGATGATTTGACGTCAT
CCCCACCTTCCTCCGGTTTATCACCGGCAGTCTGATATGAGTCCTCAAC
TCAATGTTAGTAACATATCACAAGGGTTGCGCTCGTTGCGGGACTTAAC
CCAACATCTCACGACACGAGCTGACGACAACCATGCACCACCTGTCTCC
TTGATAACCTCGGATATATCTCTATACCTCTGCAAGGGATGTCAAGGCC
TGGTAAGGTTCTTCGCGTTGCTTCGAATTAAACCACATACTCCACCGCT
TGTGCGGGCCCCCGTCAATTCCTTTGAGTTTCACACTTGCGTGCATACT
CCCCAGGCGGAGAACTTATTGCGTTAACTGCGGCACTGAGTTATTCCCC
CAACACCTAGTTCTCATCGTTTACGGCGTGGACTACTAGGGTATCTAAT
CCTATTTGCTCCCCACGCTTTCGTGCTTCAGTGTCAGAATCCAGACCAG
ACGGCCGCCTTCGCCACCGGTGTTCTTCCATATATCTACGCATTTTACC
GCTACACATGGAGTTCCGCCGTCCTCTTCTGTTCTCTAGCTGATCAGTT
TCCAGAGCAAGTACGGGTTGAGCCCATACCTTTTACTCCAGACTTGATC
TGCCACCTACGCACCCTTTACGCCCAATCATTCCGGATAACGCTCGCCA
CCTACGTATTACCGCGGCTGCTGGCACGTAGTTAGCCGTGACTTTCTGG
TAAGATACCATCACTCACTCATCATTCCCTATGAGTGCCGTTTTTCTCT
TACAACAGAGCTTTACGATCCGAAGACCTTCCTCACTCACGCGGCATTG
CTCGTTCAGGGTTCCCCCCATTGACGAAAATTCCCTACTGCTGCCTCCC
GTAGGAGTTTGGGCCGTGTCTCAGTCCCAATGTGGCCGTCCGCCCTCTC
AGGCCGGCTATGCATCGTCGCCTTGGTGGGCCGTTACCTCACCAACTAG
CTAATGCACCGCAGGTCCATCCATGTTCATGGCCTTAGCCACTTTAATA
GCAGTCAAATGCTTGTCTGCTACCTATCCGGTTTTAGCATCCGTTTCCA
GAAGTTATCCCGGGCACATGGGCAGGTTACCTACGTGTTACTCACCCGT
TCGCCACTAGATTTAGGAAAGCAAGCTTTCCTTCCTCTCGTTC
```

The specific growth of this strain was optimised for future assays using the one recommended by the DSMZ culture collection. The medium consisted of minced meat (Chopped meat medium) (DSMZ Medium 78) supplemented with 0.1% tween 80.

Example 2. Selection of *H. biformis* Based on its Capacity to In Vitro Modulate Inflammation In vitro assays were carried out in order to comparatively evaluate the immunomodulatory properties of the collection of bacterial isolates and thus select the bacterium capable of inducing the greatest anti-inflammatory response in classical monocytes, and therefore, with potential therapeutic interest in the treatment of inflammation associated with obesity and the alteration in glucose metabolism. To this end, cell suspensions of different bacteria were used as a stimulus of cultures of peripheral blood mononuclear cells (PBMCs) and the number of classical monocytes and the levels of the anti-inflammatory cytokine IL-4 with respect to the pro-inflammatory cytokine IFNγ were measured by flow cytometry.

Cultivation and Stimulation of PBMCs

From whole blood of healthy volunteers, Peripheral Blood Mononuclear Cells (PBMCs) were isolated using a Ficoll gradient (Ficoll Paque-Plus 17-1440-02, Bioscience). After treating them with a solution to lyse erythrocytes (Lysis Buffer for Red Blood Cells, RBC, Miltenyi Biotec., Spain) they were resuspended in RPMI 1640 medium (Gibco, Barcelona, Spain) supplemented with 10% foetal bovine serum (Gibco, Barcelona, Spain), streptomycin (100 μg/ml, Sigma), penicillin (100 U/ml, Sigma) and L-glutamine (Sigma). To perform the experiments, the PBMCs were incubated at a concentration of 10⁶ per ml in 24-well flat-bottom polystyrene plates (Corning, Madrid, Spain) at 37° C., at 5% $CO_2$. Suspensions of live bacteria were used as a stimulus at a concentration of 10⁷ cfu/ml. Purified lipopolysaccharide (LPS) from *Salmonella enterica* serotype *Typhimurium* (Sigma Chemical Co, Madrid, Spain) was used as a positive control at a concentration of 1 μg/ml and untreated PBMC samples were used as negative control. The stimulation time was 24 hours at 37° C., at 5% $CO_2$. After this time elapsed, the cells were collected and centrifuged, separating the cell pellet from the supernatant. Each type of stimulus was assayed in triplicate in 3 independent experiments. The culture supernatants were fractionated and stored in aliquots at −80° C.

Characterisation of the Immunomodulatory Properties of Isolated Bacterial Strains on PBMCs by Flow Cytometry The stimulated PBMCs were analysed by flow cytometry in order to determine the levels of classical pro-inflammatory monocytes, using the markers CD14 and CD16. Furthermore, pro-inflammatory cytokine IFNγ levels and anti-inflammatory cytokine IL-4 levels in monocytes were evaluated. To this end, the cells were permeabilised and fixed (Fixation/Permeabilization Solution Kit, BD-Bioscience) and resuspended with the FACS solution (PBS1×+ BSA 0.2%). Marker levels were measured using BD LSR-Fortessa.

From the collection of isolated bacteria, the strain of the invention *Holdemanella biformis* CECT 9752 was the one which induced the most significant immunomodulatory effects, inducing a higher production of the anti-inflammatory cytokine IL-4 with respect to the pro-inflammatory IFNγ (higher IL-4/IFNγ) and a reduction of classical pro-inflammatory monocytes (CD14++CD16−) with respect to untreated and LPS-treated cells (Table 1). This strain was selected in order to evaluate the ability thereof to prevent alterations in glucose metabolism in an animal model of obesity (Example 3).

TABLE 1

In vitro characterisation of the immunomodulatory properties of the bacterial isolates on PBMCs. The results are expressed as the mean and standard error (in parenthesis) of the relative levels of classical monocytes and the IL-4/IFNγ ratio measured by flow cytometry. Significant differences (P < 0.05) between groups were established by means of one-way ANOVA, followed by the Tukey test. Different letters indicate significant differences between experimental groups.

| Bacterial strains | Classical Monocytes | IL-4/IFNγ |
|---|---|---|
| Untreated | 0.70(0.02)b | 1.74(0.24)c |
| LPS | 1.00(0.05)a | 0.80(0.05)d |
| *Flavonifractor plautii* A33 | 0.63(0.06)c | 2.67(0.20)b |
| *Ezakiella peruensis* C260 | 0.59(0.06)c | 2.91(0.27)b |
| *Holdemanella biformis* G59 | 0.43(0.02)d | 5.45(0.09)a |
| *Alistipes shahii* DTA14 | 0.67(0.05)c | 2.51(0.14)b |
| *Eubacterium cylindroides* G20 | 0.75(0.04)b | 1.61(0.10)c |
| *Pseudoflavonifractor capillosus* H28 | 0.87(0.04)b | 1.48(0.06)c |

Example 3. Characterisation of the Effects of *H. biformis* in the Regulation of Energy and Glucose Metabolism in an Animal Model of Obesity Development of the Animal Model of Obesity and Sampling Adult male C57BL/6 mice (6-8 weeks, Charles River, Les Oncins, France), kept under controlled temperature (23° C.), relative humidity (40-50%) and 12-hour light/dark cycle conditions, were fed a high-calorie diet (HFHSD; D12451, Research diet, Brogaarden, Denmark) rich in fat (45% Kcal) and sucrose (17% Kcal) or a control diet with standard fat content and without sucrose (CD, 10% Kcal from fat; D12450K, Research diet, Brogaarden, Denmark) for 14 weeks. Daily, the mice fed the HFHSD diet received an oral dose of the bacterial strain object of the invention ($1×10^8$ colony-forming units [CFU]) suspended in 10% skim milk. The carrier or placebo (10% skim milk) was administered in the same way to both the control group with the obese phenotype (HFHSD) and the control group with the lean phenotype (CD) (n=10 mice per group). After 14 weeks, the mice were slaughtered by cervical dislocation in order to obtain biological samples (blood, intestine, liver, etc.).

Characterisation of the Metabolic Phenotype

Fasting basal blood glucose (week 8 and 10) was determined from blood from the saphenous vein using glucose test strips (Contour XT Bayer, Barcelona, Spain) and the oral glucose tolerance using an oral glucose test (OGTT, week 10) in which blood glucose was measured at 15, 30, 60 and 120 minutes after having administered an oral glucose overload (2 g/Kg) to mice subjected to 4 hours of fasting. Plasma levels of insulin and gastrointestinal hormones such as the glucagon-like peptide 1 (GLP-1) and peptide YY (PYY) were also measured by multiplex (Mouse Metabolic Magnetic Beads Panel, Merck Chemicals and Life Science, Madrid, Spain).

Figure 1B:
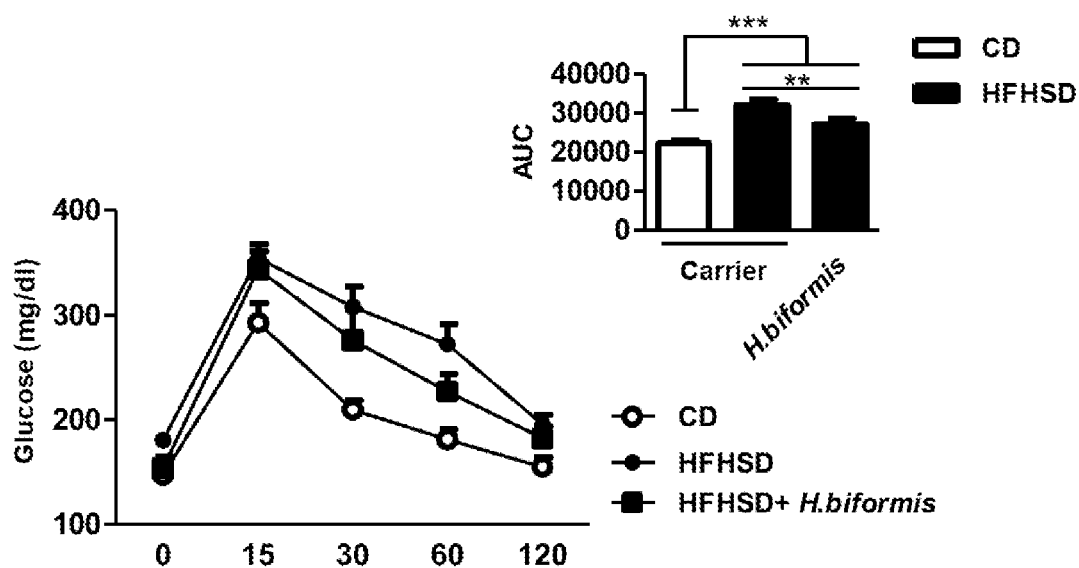
Figure 2A:
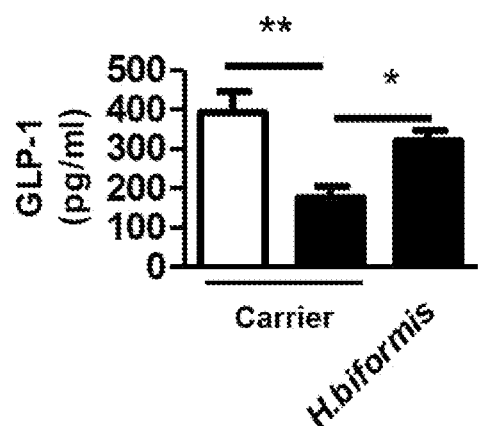
FIGS. 2A-2B: Effect of the administration of the strain H. biformis CECT 9752 ($1 \times 10^8$ cfu/day) to obese C57BL/6 mice (n=10/group) for 14 weeks on the levels of GLP1 and PYY in plasma. (a) levels of GLP-1 (Glucagon-like peptide) and (b) PYY (Peptide YY) in pg/ml. The data are represented as means and standard error. Statistically significant differences were established by applying one-way ANOVA followed by the Tukey test (p<0.05). CD, control diet; HFHSD, high-fat diet.
Figure 2B:
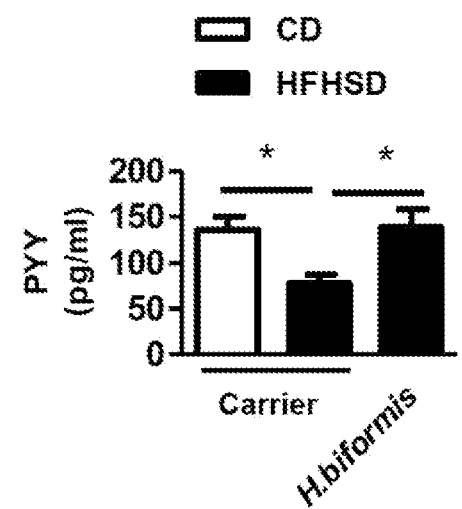

The bacterium object of the invention was able to improve both basal blood glucose (FIG. 1A) and oral tolerance to glucose (FIG. 1B). According to these results, the bacterium also increased the levels of the gastrointestinal hormones GLP-1 and PYY which control postprandial blood glucose levels by stimulating insulin secretion and reducing intake.

Analysis of Energy Metabolism in the Liver

Taking into account the importance of the liver in maintaining blood glucose, energy metabolism in this tissue was also examined. To this end, by using qPCR, the mRNA levels of the enzymes which limit glucidic and lipid metabolism were analysed, such as: kinase which facilitates the storage of glucose in the form of glycogen under anabolic conditions (glycogenesis; Gck, glucokinase); the catabolic unit of glucose-6 phosphatase (G6Pc) and phosphoenolpyruvate carboxylase 1 (PcK1), both involved in gluconeogenesis; lipase which modulates the homeostasis of triglycerides (Tg) in plasma (lipoprotein lipase, LpL); acetyl-CoA carboxylase (ACC) and fatty acid synthetase (FAS), both enzymes involved in lipogenesis, hormone-sensitive lipase (HSL) which hydrolyses the TG (lipolysis) and carnitine palmitoyltransferase, enzyme which limits the β-oxidation of fatty acids. The total RNA was isolated using TRIsure reagent according to instructions from the manufacturer (Bioline, Luckenwalde). Reverse transcription was performed with 2 μg of total RNA using High-Capacity cDNA Reverse Transcription Kit (California, USA). The cDNA (ng of cDNA detailed in Table 2) was amplified by qPCR with LightCycler® 480 SYBR Green I Master (Mannheim, Germany) and forward (F) and reverse (R) primers (sequences shown in Table 2) in the Roche Light Cycler 480 equipment (Roche, Boulogne-Billancourt, France). The relative expression of the mRNA was calculated by means of method $2^{-\Delta\Delta Ct}$.

TABLE 2

Sequence of the primers used to analyse the expression of the genes by qPCR. Glucokinase (Gck), glucose-6 phosphatase catalytic unit (G6Pc), phosphoenolpyruvate carboxylase 1 (PcK1), lipoprotein lipase (LpL), Acetyl-CoA carboxylase (ACC), Fatty Acid Synthetase (FAS), Hormone-sensitive lipase (HSL), Carnitine palmitoyltransferase (CPT1a), Glucagon-like peptide receptor (GLP-1R), and Peptide YY (PYY).

| Gen | | Sec 5'-3 |
|---|---|---|
| G6Pc | F | TTACCAAGACTCCCAGGACTG (SEQ ID NO: 4) |
| | R | GAGCTGTTGCTGTAGTAGTCG (SEQ ID NO: 5) |
| GcK | F | ATGTGAGGTCGGCATGATTGT (SEQ ID NO: 6) |
| | R | CCTTCCACCAGCTCCACATT (SEQ ID NO: 7) |
| PCK1 | F | AGCCTTTGGTCAACAACTGG (SEQ ID NO: 8) |
| | R | TGCCTTCGGGGTTAGTTATG (SEQ ID NO: 9) |
| LPL | F | TGAAAGCCGGAGAGACTCAG (SEQ ID NO: 10) |
| | R | AGTGTCAGCCAGACTTCTTCAG (SEQ ID NO: 11) |
| ACC | F | TAATGGGCTGCTTCTGTGACTC (SEQ ID NO: 12) |
| | R | CTCAATATCGCCATCAGTCTTG (SEQ ID NO: 13) |
| FAS | F | GGAGGTGGTGATAGCCGGTAT (SEQ ID NO: 14) |
| | R | TGGGTAATCCATAGAGCCCAG (SEQ ID NO: 15) |
| HSL | F | ATGCCACTCACCTCTGATCC (SEQ ID NO: 16) |
| | R | CTGTCCTGTCCTTCCCGTAG (SEQ ID NO: 17) |
| CPT1a | F | TTTGAATCGGCTCCTAATGG (SEQ ID NO: 18) |
| | R | CCCAAGTATCCACAGGGTCA (SEQ ID NO: 19) |
| GLP-1R | F | GGCGTCAACTTTCTTATCTTC (SEQ ID NO: 20) |
| | R | CAAAGATGACTTCATGTGTCC (SEQ ID NO: 21) |
| peripherin | F | ATCTCAGTGCCGGTTCATTC (SEQ ID NO: 22) |
| | R | GGGCCAAGCTTAGGAATAGG (SEQ ID NO: 23) |
| proglucagon | F | CAAACCAAGATCACTGACAAGAAAT (SEQ ID NO: 24) |
| | R | GGGTTACACAATGCTAGAGGGA (SEQ ID NO: 25) |
| PYY | F | CTTCACAGACGACAGCGACA (SEQ ID NO: 26) |
| | R | GGGAAATGAACACACACAGCC (SEQ ID NO: 27) |

F = forward; R = reverse.

The study of the expression of these enzymes in the liver revealed significant effects on the energy metabolism of the obese mice, in particular, a reduction in the expression of LpL and ACC and an increase in the mRNA levels of CPT1a were observed (FIG. 3). The bacterium prevented the hepatic overexpression of CPT1a in obese mice reaching the levels of control mice fed with the control diet; however, it did not produce significant effects on the expression of LpL and ACC. This result together with the decreased expression of ACC suggests that the obese mice to which the bacterium is administered may have reduced levels of malonyl-CoA, a metabolite derived from glucose metabolism which inhibits CPT1a, thus increasing the oxidation of fatty acids. The improvement in the glucose uptake by peripheral tissues induced by the bacterium (FIGS. 1A and 1B) is associated with the normalisation of the oxidation of fatty acids. The bacterium, furthermore, tends to decrease, although not significantly, the mRNA levels of G6Pc, enzyme which limits glucose production.

Figure 4C:
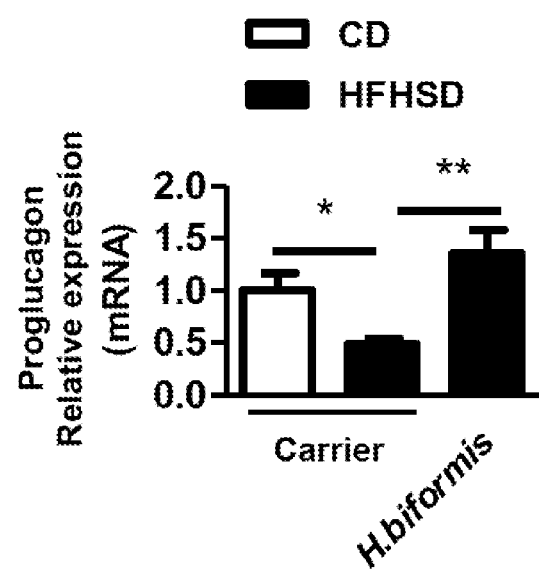

Identification of Intestinal Signals Mediating the Effects of the Bacterium on Glucose Tolerance The expression levels of the neuronal marker peripherin in the intestine were analysed, which could indicate that the bacterium acts by an intestine-brain-liver mechanism and through the stimulation of vagal afferents and GLP-1R (located in the vagal afferent fibres) in the ileum. Although the obese mice did not show significant changes in the expression of peripherin or GLP-1R in the ileum with respect to the control group (FIGS. 4A and 4B, respectively), the bacterium increased the expression of peripherin up to 8 times and that of GLP-1R twice, which suggests that the increase in GLP-1 induced by the bacterium could be stimulating the intestine-brain-liver axis, wherein the stimulation of the intestinal innervations would lead the nervous signal to the brain in order to be integrated into the hypothalamus, which would modulate the energy homeostasis through efferent fibres.

Furthermore, the obese mice presented reduced levels of proglucagon expression in the colon compared to the control mice (FIG. 4C), while the bacterium of the invention was able to prevent this reduction and normalise the mRNA levels.

The invention claimed is:

1. A method for the treatment of diseases related to alterations in glucose metabolism, comprising administering an effective amount of the strain *Holdemanella biformis* with deposit number CECT 9752, or a composition comprising the strain *Holdemanella biformis* with deposit number CECT 9752 to a subject, wherein the disease related to alterations in glucose metabolism is selected from the list consisting of glucose intolerance, insulin resistance, metabolic syndrome, type 2 diabetes, and gestational diabetes.

2. The method according to claim 1, wherein said bacterium is in the form of viable cells or in the form of non-viable cells.

3. The method according to claim 1, wherein the composition comprises, additionally, at least one microorganism different than the bacterium of the genus *Holdemanella*.

4. The method according to claim 1, wherein the composition is a pharmaceutical composition.

5. The method according to claim 4, wherein the composition comprises, additionally, at least one pharmaceutically acceptable carrier and/or excipient.

6. The method according to claim 1, wherein the composition is a nutritional composition.

7. The method according to claim 6, wherein the nutritional composition is a food, a supplement, a nutraceutical, a probiotic or a symbiotic.

8. The method according to claim 1, wherein the composition has a strain concentration of between $10^3$ and $10^{14}$ colony-forming units (cfu) per gram or millilitre of final composition.

* * * * *

SEQUENCE LISTING

<160> NUMBER OF SEQ ID NOS: 27

<210> SEQ ID NO 1
<211> LENGTH: 20
<212> TYPE: DNA

```
<213> ORGANISM: Artificial Sequence
<220> FEATURE:
<223> OTHER INFORMATION: Primer 27F

<400> SEQUENCE: 1
agagtttgat cctggctcag                                                 20

<210> SEQ ID NO 2
<211> LENGTH: 17
<212> TYPE: DNA
<213> ORGANISM: Artificial Sequence
<220> FEATURE:
<223> OTHER INFORMATION: Primer 1401r

<400> SEQUENCE: 2
cggtgtgtac aagaccc                                                    17

<210> SEQ ID NO 3
<211> LENGTH: 1268
<212> TYPE: DNA
<213> ORGANISM: Holdemanella biformis

<400> SEQUENCE: 3
cttcatgaag tcgggttgca gacttcaatc cgaactgaga cgtcctttat gagattcgct     60
tgccttcaca ggcttgccgc tctttgtaga cgccattgta gtacgtgtgt agcccaggcc    120
ataaggggca tgatgatttg acgtcatccc caccttcctc cggtttatca ccggcagtct    180
gatatgagtc ctcaactcaa tgttagtaac atatcacaag ggttgcgctc gttgcgggac    240
ttaacccaac atctcacgac acgagctgac gacaaccatg caccacctgt ctccttgata    300
acctcggata tatctctata cctctgcaag ggatgtcaag gcctggtaag gttcttcgcg    360
ttgcttcgaa ttaaaccaca tactccaccg cttgtgcggg ccccgtcaa ttcctttgag     420 tttcacactt gcgtgcatac tccccaggcg gagaacttat tgcgttaact gcggcactga    480
gttattcccc caacacctag ttctcatcgt ttacggcgtg gactactagg gtatctaatc    540
ctatttgctc cccacgcttt cgtgcttcag tgtcagaatc cagaccagac ggccgccttc    600
gccaccggtg ttcttccata tatctacgca ttttaccgct acacatggag ttccgccgtc    660
ctcttctgtt ctctagctga tcagtttcca gagcaagtac gggttgagcc catacctttt    720
actccagact tgatctgcca cctacgcacc ctttacgccc aatcattccg gataacgctc    780
gccacctacg tattaccgcg gctgctggca cgtagttagc cgtgactttc tggtaagata    840
ccatcactca ctcatcattc cctatgagtg ccgttttcct cttacaacag agctttacga    900
tccgaagacc ttcctcactc acgcggcatt gctcgttcag ggttcccccc attgacgaaa    960
attccctact gctgcctccc gtaggagttt gggccgtgtc tcagtcccaa tgtggccgtc   1020
cgccctctca ggccggctat gcatcgtcgc cttggtgggc cgttacctca ccaactagct   1080
aatgcaccgc aggtccatcc atgttcatgg ccttagccac tttaatagca gtcaaatgct   1140
tgtctgctac ctatccggtt ttagcatccg ttttccagaag ttatcccggg cacatgggca  1200
ggttacctac gtgttactca cccgttcgcc actagattta ggaaagcaag ctttccttcc   1260
tctcgttc                                                            1268

<210> SEQ ID NO 4
<211> LENGTH: 21
<212> TYPE: DNA
<213> ORGANISM: Artificial Sequence
<220> FEATURE:
<223> OTHER INFORMATION: Forward primer G6Pc
```

<400> SEQUENCE: 4
ttaccaagac tcccaggact g                                              21

<210> SEQ ID NO 5
<211> LENGTH: 21
<212> TYPE: DNA
<213> ORGANISM: Artificial Sequence
<220> FEATURE:
<223> OTHER INFORMATION: Reverse primer G6Pc

<400> SEQUENCE: 5
gagctgttgc tgtagtagtc g                                              21

<210> SEQ ID NO 6
<211> LENGTH: 21
<212> TYPE: DNA
<213> ORGANISM: Artificial Sequence
<220> FEATURE:
<223> OTHER INFORMATION: Forward primer GcK

<400> SEQUENCE: 6
atgtgaggtc ggcatgattg t                                              21

<210> SEQ ID NO 7
<211> LENGTH: 20
<212> TYPE: DNA
<213> ORGANISM: Artificial Sequence
<220> FEATURE:
<223> OTHER INFORMATION: Reverse primer GcK

<400> SEQUENCE: 7
ccttccacca gctccacatt                                                20

<210> SEQ ID NO 8
<211> LENGTH: 20
<212> TYPE: DNA
<213> ORGANISM: Artificial Sequence
<220> FEATURE:
<223> OTHER INFORMATION: Forward primer PCK1

<400> SEQUENCE: 8
agcctttggt caacaactgg                                                20

<210> SEQ ID NO 9
<211> LENGTH: 20
<212> TYPE: DNA
<213> ORGANISM: Artificial Sequence
<220> FEATURE:
<223> OTHER INFORMATION: Reverse primer1 PCK

<400> SEQUENCE: 9
tgccttcggg gttagttatg                                                20

<210> SEQ ID NO 10
<211> LENGTH: 20
<212> TYPE: DNA
<213> ORGANISM: Artificial Sequence
<220> FEATURE:
<223> OTHER INFORMATION: Forward primer LpL

<400> SEQUENCE: 10
tgaaagccgg agagactcag                                                20

<210> SEQ ID NO 11

```
<211> LENGTH: 22
<212> TYPE: DNA
<213> ORGANISM: Artificial Sequence
<220> FEATURE:
<223> OTHER INFORMATION: Reverse primer LpL

<400> SEQUENCE: 11
agtgtcagcc agacttcttc ag                                              22

<210> SEQ ID NO 12
<211> LENGTH: 22
<212> TYPE: DNA
<213> ORGANISM: Artificial Sequence
<220> FEATURE:
<223> OTHER INFORMATION: Forward primer ACC

<400> SEQUENCE: 12
taatgggctg cttctgtgac tc                                              22

<210> SEQ ID NO 13
<211> LENGTH: 22
<212> TYPE: DNA
<213> ORGANISM: Artificial Sequence
<220> FEATURE:
<223> OTHER INFORMATION: Reverse primer ACC

<400> SEQUENCE: 13
ctcaatatcg ccatcagtct tg                                              22

<210> SEQ ID NO 14
<211> LENGTH: 21
<212> TYPE: DNA
<213> ORGANISM: Artificial Sequence
<220> FEATURE:
<223> OTHER INFORMATION: Forward primer FAS

<400> SEQUENCE: 14
ggaggtggtg atagccggta t                                               21

<210> SEQ ID NO 15
<211> LENGTH: 21
<212> TYPE: DNA
<213> ORGANISM: Artificial Sequence
<220> FEATURE:
<223> OTHER INFORMATION: Reverse primer FAS

<400> SEQUENCE: 15
tgggtaatcc atagagccca g                                               21

<210> SEQ ID NO 16
<211> LENGTH: 20
<212> TYPE: DNA
<213> ORGANISM: Artificial Sequence
<220> FEATURE:
<223> OTHER INFORMATION: Forward primer HSL

<400> SEQUENCE: 16
atgccactca cctctgatcc                                                 20

<210> SEQ ID NO 17
<211> LENGTH: 20
<212> TYPE: DNA
<213> ORGANISM: Artificial Sequence
<220> FEATURE:
<223> OTHER INFORMATION: Reverse primer HSL

<400> SEQUENCE: 17
```

```
ctgtcctgtc cttcccgtag                                               20

<210> SEQ ID NO 18
<211> LENGTH: 20
<212> TYPE: DNA
<213> ORGANISM: Artificial Sequence
<220> FEATURE:
<223> OTHER INFORMATION: Forward primer CPT1a

<400> SEQUENCE: 18
tttgaatcgg ctcctaatgg                                               20

<210> SEQ ID NO 19
<211> LENGTH: 20
<212> TYPE: DNA
<213> ORGANISM: Artificial Sequence
<220> FEATURE:
<223> OTHER INFORMATION: Reverse primer CPT1a

<400> SEQUENCE: 19
cccaagtatc cacagggtca                                               20

<210> SEQ ID NO 20
<211> LENGTH: 21
<212> TYPE: DNA
<213> ORGANISM: Artificial Sequence
<220> FEATURE:
<223> OTHER INFORMATION: Forward primer GLP-1R

<400> SEQUENCE: 20
ggcgtcaact ttcttatctt c                                             21

<210> SEQ ID NO 21
<211> LENGTH: 21
<212> TYPE: DNA
<213> ORGANISM: Artificial Sequence
<220> FEATURE:
<223> OTHER INFORMATION: Reverse primer GLP-1R

<400> SEQUENCE: 21
caaagatgac ttcatgtgtc c                                             21

<210> SEQ ID NO 22
<211> LENGTH: 20
<212> TYPE: DNA
<213> ORGANISM: Artificial Sequence
<220> FEATURE:
<223> OTHER INFORMATION: Forward primer peripherin

<400> SEQUENCE: 22
atctcagtgc cggttcattc                                               20

<210> SEQ ID NO 23
<211> LENGTH: 20
<212> TYPE: DNA
<213> ORGANISM: Artificial Sequence
<220> FEATURE:
<223> OTHER INFORMATION: Reverse primer peripherin

<400> SEQUENCE: 23
gggccaagct taggaatagg                                               20

<210> SEQ ID NO 24
<211> LENGTH: 25
<212> TYPE: DNA
```

```
<213> ORGANISM: Artificial Sequence
<220> FEATURE:
<223> OTHER INFORMATION: Forward primer proglucagon

<400> SEQUENCE: 24
caaaccaaga tcactgacaa gaaat                                          25

<210> SEQ ID NO 25
<211> LENGTH: 22
<212> TYPE: DNA
<213> ORGANISM: Artificial Sequence
<220> FEATURE:
<223> OTHER INFORMATION: Reverse primer proglucagon

<400> SEQUENCE: 25
gggttacaca atgctagagg ga                                             22

<210> SEQ ID NO 26
<211> LENGTH: 20
<212> TYPE: DNA
<213> ORGANISM: Artificial Sequence
<220> FEATURE:
<223> OTHER INFORMATION: Forward primer PYY

<400> SEQUENCE: 26
cttcacagac gacagcgaca                                                20

<210> SEQ ID NO 27
<211> LENGTH: 21
<212> TYPE: DNA
<213> ORGANISM: Artificial Sequence
<220> FEATURE:
<223> OTHER INFORMATION: Reverse primer PYY

<400> SEQUENCE: 27
gggaaatgaa cacacacagc c                                              21
```